United States Patent
Lundin et al.

(10) Patent No.: US 10,101,239 B2
(45) Date of Patent: Oct. 16, 2018

(54) SYSTEM AND METHOD FOR DETERMINING THE INTEGRITY OF CONTAINERS BY OPTICAL MEASUREMENT

(71) Applicant: GASPOROX AB, Lund (SE)

(72) Inventors: Patrik Lundin, Harlösa (SE); Daniel Karlsson, Lund (SE); Märta Lewander Xu, Lund (SE); Johannes Swartling, Lund (SE); Joachim Dillner, Tumba (SE)

(73) Assignee: GASPOROX AB, Lund (SE)

( * ) Notice: Subject to any disclaimer, the term of this patent is extended or adjusted under 35 U.S.C. 154(b) by 0 days.

(21) Appl. No.: 15/563,255

(22) PCT Filed: Apr. 4, 2016

(86) PCT No.: PCT/EP2016/057382
§ 371 (c)(1),
(2) Date: Sep. 29, 2017

(87) PCT Pub. No.: WO2016/156622
PCT Pub. Date: Oct. 6, 2016

(65) Prior Publication Data
US 2018/0095000 A1    Apr. 5, 2018

(30) Foreign Application Priority Data

Apr. 2, 2015  (SE) .................................... 1530046

(51) Int. Cl.
*G01N 21/00*    (2006.01)
*G01M 3/22*    (2006.01)
(Continued)

(52) U.S. Cl.
CPC ............. *G01M 3/229* (2013.01); *G01L 11/02* (2013.01); *G01M 3/3281* (2013.01); *G01M 3/38* (2013.01);
(Continued)

(58) Field of Classification Search
CPC ............. G01N 21/3504; G01N 21/718; G01N 2021/399; G01N 21/1717; G01N 21/359;
(Continued)

(56) References Cited

FOREIGN PATENT DOCUMENTS

| WO | 2010145892 A1 | 12/2010 |
|----|---------------|---------|
| WO | 2012001633 A2 | 1/2012  |

(Continued)

OTHER PUBLICATIONS

International Search Report for corresponding application PCT/EP2016/057382 dated Jul. 15, 2016.
(Continued)

*Primary Examiner* — Tri T Ton
(74) *Attorney, Agent, or Firm* — Norris McLaughlin, PA

(57) ABSTRACT

A method and system is disclosed for determining the integrity of a closed container. The method and system includes the steps of positioning the container in a surrounding, changing a gas pressure, a gas composition, a gas concentration, or any combination of gas pressure, gas concentration and gas composition, in the surrounding. Thereafter subjecting the container to an optical sensor, non-intrusively, the sensor being sensitive to at least one gas, and the sensor is configured for detecting the at least one gas inside the container. Reading a signal from the optical sensor related to a gas pressure, a gas concentration, a gas composition, or any combination of gas pressure, gas concentration, and gas composition, inside the container. The behavior of the signal being indicative of breach in integrity of the container.

20 Claims, 6 Drawing Sheets

(51) Int. Cl.
*G01L 11/02* (2006.01)
*G01M 3/32* (2006.01)
*G01M 3/38* (2006.01)
*G01N 21/3504* (2014.01)
*G01N 21/39* (2006.01)
*G01N 21/71* (2006.01)
*G01N 21/17* (2006.01)
*G01N 21/90* (2006.01)
*G01N 21/359* (2014.01)
*G01N 21/65* (2006.01)

(52) U.S. Cl.
CPC ..... *G01N 21/1717* (2013.01); *G01N 21/3504* (2013.01); *G01N 21/39* (2013.01); *G01N 21/718* (2013.01); *G01N 21/359* (2013.01); *G01N 21/65* (2013.01); *G01N 21/90* (2013.01); *G01N 2021/399* (2013.01)

(58) Field of Classification Search
CPC ........ G01N 21/39; G01N 21/90; G01N 21/65; G01L 11/02; G01M 3/229; G01M 3/3281; G01M 3/38
USPC .................................................. 356/432–444
See application file for complete search history.

(56) References Cited

FOREIGN PATENT DOCUMENTS

| | | |
|---|---|---|
| WO | 2014191438 A1 | 12/2014 |
| WO | 2015121064 A1 | 8/2015 |
| WO | 2016051341 A1 | 4/2016 |
| WO | 2016156622 A1 | 10/2016 |

OTHER PUBLICATIONS

Written Opinion of the International Searching Authority for corresponding application PCT/EP2016/057382 dated Jul. 15, 2016.

SYSTEM AND METHOD FOR DETERMINING THE INTEGRITY OF CONTAINERS BY OPTICAL MEASUREMENT

This application is a § 371 U.S. National stage of PCT International Patent Application No. PCT/EP2016/057382, filed Apr. 4, 2016, which claims foreign priority benefit of Swedish Patent Application No. SE 1530046-0, filed Apr. 2, 2015, the disclosures of each of which patent applications are incorporated herein by reference.

BACKGROUND OF THE INVENTION

Field of the Invention

This disclosure pertains to determining the integrity of closed containers, by subjecting said containers to variations in outside atmosphere and performing optical measurements on the container for detection of gas inside said container. Especially, the disclosure relates to non-destructive leak testing of containers such as packages.

Description of the Prior Art

Verification of the integrity of sealed containers is important in many industrial settings. Examples include quality control of packaging of products such as food and pharmaceuticals. The integrity of sealed containers may be compromised e.g. by deficiencies in the sealing process, or in the barrier materials, or due to damage during the production process or handling. Integrity is important for several reasons, e.g., to keep the contents of the package inside the container; to keep any pre-filled gas composition inside the container at desired levels; and to keep outside atmospheric gases from entering the container. The last two points may be of great importance to prevent degradation of the contents of the container. For example, the level of oxygen or water vapour (moist) often determines the shelf life of the product. Other motivations for detecting leaks in containers are to verify the integrity of the container to substances other than gas, e.g., including but not limited to water, liquids, bacteria, viruses and other biological agents. By using gas-based leak detection, a measure of the size of a leak can be obtained, which is relevant to the integrity against these other substances.

Several means to verify the integrity of containers are known in the art. For example, flexible containers may be subjected to mechanical force to check the resistance of the pressure of the gas inside. However, this method is typically not suitable for detection of small leaks, and also carries the risk of damaging the container. Some types of containers can be inspected by automated vision systems to detect anomalies, but again this may not detect small leaks, and the method is limited to certain kinds of containers. Small leaks can be detected by penetration tests using dyes or trace gases such as helium, but such tests are often destructive. Another method is to subject the container to external variations in the outside atmosphere, e.g., by placing it in a (partial) vacuum chamber, or exerting overpressure on the container with atmospheric air or other gases, or combinations of these techniques. With this method, some additional means to detect a leak of a container is required, i.e., by controlling or measuring one or more parameters that may change as consequence of the variation in outside pressure or gas composition, if a leak is present. Several such techniques are known in the art. For example, transient pressure variation in the chamber may be recorded, and its behaviour may be indicative of a leak in the sample. As another example, if the container contains a gas species that is not present in normal air at significant concentrations, a gas detector may be placed in the test chamber (or at the outlet) to detect the presence of that gas species, indicating a leak.

Non-intrusive optical detection of gases inside packages for the purpose of quality control is disclosed in patent EP 10720151.9 (Svanberg et al.). The principle of optical detection of the gas in the headspace of packages for the purpose of indicating leaks is known in the art. This method is based on that the gas inside the package may deviate from an assumed gas composition due to interaction with the surrounding atmosphere through the leak. However, in normal atmosphere, for small leaks, it may take a very long time before there is a detectable deviation of the gas composition inside a package, which makes the method impractical in many situations.

There are situations where none of the methods previously described in the art are suitable for detecting a leak. Examples include, but are not limited to, when the volume of gas inside the container is very small, or in certain cases where the gas inside the container is normal air. Hence, new improved apparatus and methods for detecting leaks in such containers would be advantageous.

SUMMARY OF THE DISCLOSURE

Accordingly, embodiments of the present disclosure preferably seek to mitigate, alleviate or eliminate one or more deficiencies, disadvantages or issues in the art, such as the above-identified, singly or in any combination by providing a device, system or method according to the appended patent claims for non-destructively determining the integrity of sealed containers, by subjecting said containers to variations in outside atmosphere and performing optical measurements on the container.

The disclosure generally comprises the combination of two parts, where the first part consists of subjecting the container to variations in outside pressure or gas composition, such as by placing it in a (partial) vacuum or underpressure, or exerting overpressure on the container with atmospheric air or other gases, or combinations of these steps. The purpose of this first part is to impose change to the concentration, or composition, or pressure, of the gas or gases inside the container as result of any leaks in the container. The second part consists of subjecting the container to optical spectroscopic measurement of the gas or gases inside the container, with the purpose of detecting any variation in the optical signal arising as consequence of the leak as opposed to the signal where no leak is present. Such difference in signal could be due to, but is not limited to, a decreased or increased concentration of at least one gas inside the container as result of the leak, or a variation in the gas pressure inside the container, or the introduction of a new gas species inside the container due to the leak.

In a first aspect, a method of determining the integrity of a closed container is disclosed. The method comprising positioning said container in a surrounding, then changing a gas pressure, a gas composition, a gas concentration, or any combination of gas pressure, gas concentration and gas composition, in the surrounding. Subjecting the container to an optical sensor, non-intrusively, the sensor being sensitive to at least one gas, and the sensor is configured for detecting the at least one gas inside the container. Reading a signal from the optical sensor related to a gas pressure, a gas concentration, a gas composition, or any combination of gas pressure, gas concentration, and gas composition, inside the container. The behaviour of the signal is indicative of breach in integrity of the container.

In an example of the disclosure, the method includes applying a vacuum or underpressure in the surrounding.

An advantage with applying vacuum or underpressure is to increase the diffusion of gas from inside the container to outside. A detected decrease of the gas inside the container means that there may be a leakage.

In an example of the disclosure, the method includes applying an overpressure in the surrounding.

An advantage with applying overpressure is to increase the diffusion by forcing a gas into the container. The gas may be a gas not previously present in the container. If the new gas is detected inside the container there may be a leakage. Alternatively and/or additionally, a gas already present in the container may be applied. If an increase of the gas concentration is detected inside the container there may be a leakage.

Also, some containers handle overpressure better than underpressure with minimal deformation to the container, and vice versa. Deformation to the containers should preferably be avoided when performing measurements.

In an example of the disclosure, the method includes applying a gas or mix of gases in the surrounding.

An advantage of applying a mix of at least two gases is, for example, that an improved sensitivity in detecting leakage may be achieved. Also, by measuring on at least two gases having different diffusion rates the size of the leakage may be estimated.

A similar technique may be utilized by applying a single gas different from the gas inside the container and measuring the concentration of both gases inside the container. By measuring on both gases the sensitivity of detecting a leakage may be increased. Also, if the gases diffuse in and out of the container with different rates, the size of the leakage may be estimated.

Another advantage of applying a gas outside the container is that the container may be exerted to a minimum of stress or strain due to an applied underpressure or overpressure that may deform the container. In an example of the disclosure, the method includes applying any combination of the steps of applying an overpressure, an underpressure, at least one gas, or mix of gas in sequence in the surrounding.

By using a combination of steps an increased difference in the measured signal may be obtained. For example, by first creating an underpressure in the surrounding an underpressure may be obtained in the container which may increase the diffusion of an applied gas or mix of gases. An even larger diffusion may be obtained by first applying an underpressure and then applying a gas or a mix of gases together with an overpressure.

By utilizing a combination of steps the leakage may be easier characterized, for example through detection of the propagation of an overpressure or an underpressure, and the diffusion of a gas or mix of gases.

Alternatively and/or additionally, a first gas or mix of gases may be applied to the surrounding and the change in signal is detected, thereafter is a second gas or mix of gases applied to the surrounding and the change in signal is again detected. Differences in properties, such as size or dipole moment, between different molecules may effect how the molecules diffuse through holes and passages. This may be utilized to detect a leakage and to characterize the leakage.

In an example of the method, the optical sensor is based on any spectroscopic or optical means of gas detection.

In an example of the method, the optical sensor is based on tunable diode laser absorption spectroscopy (TDLAS).

In an example of the method, the optical sensor is based on gas in scattering media absorption spectroscopy (GASMAS).

In an example of the method, a reference container which is known not to have leaks, or to have leaks of known characteristics, is used to provide a baseline signal, and the difference in optical signal compared to the baseline signal is used to detect leaks in subsequent containers.

As different types of containers may handle underpressure and overpressure differently it may be advantageous to use a reference container for detection of a leakage. By using a reference container a calibration for obtaining absolute values is not needed, instead the test is a comparison of the detected signal from the container compared to a detected signal from the reference container. A difference in the measured signals may indicate that there is a leakage.

This type of test may increase the robustness of the detection and/or monitoring. For example, this may be advantageous when performing inline measurements.

In an example of the method, the variation in optical signal from one time to another on the same container is used to detect a leak.

By studying the process over time, changes in the leakage may be detected. It may also be used to detect small leakages.

In an example of the method, the concentration of gas inside the container is determined.

In an example of the method, the absolute or relative pressure of at least one gas inside the container is determined.

Detection of the pressure of at least one gas inside the container may for some gases give a larger signal than measuring a difference in concentration. Hence for some gases detecting pressure may increase the sensitivity and robustness of the detection and/or monitoring.

In an example of the method, a measure of the size of a leakage is determined by measuring continuously or repeatedly an optical signal and determining the rate of change of the signal.

In a further aspect of the disclosure, a system for determining the integrity of a sealed container, the system comprises a surrounding configured for positioning the container. The surrounding is configured for changing a gas pressure, a gas composition, a gas concentration, or any combination of gas pressure, gas concentration, and gas composition. The system includes a non-intrusive optical sensor sensitive to at least one gas, and the sensor is configured for detecting the at least one gas inside the container. The system further includes a control unit for reading a signal from the optical sensor related to a gas pressure, a gas concentration, a gas composition, or any combination of gas pressure, gas concentration, and gas composition, inside the container. The behaviour of the signal is indicative of breach in integrity of the container.

In an example of the system, a vacuum or underpressure is applied in the surrounding.

In an example of the system, an overpressure is applied in the surrounding.

In an example of the system, a gas or mix of gases is applied in the surrounding.

In an example of the system, any combination of the steps of applying an overpressure, an underpressure, at least one gas, or mix of gas in sequence in the surrounding is applied in sequence.

In an example of the system, the optical sensor is based on any spectroscopic or optical means of gas detection.

In an example of the system, the optical sensor is based on tunable diode laser absorption spectroscopy (TDLAS).

In an example of the system, the optical sensor is based on gas in scattering media absorption spectroscopy (GAS-MAS).

In an example of the system, a reference container which is known not to have leaks, or to have leaks of known characteristics, is used to provide a baseline signal, and the difference in optical signal compared to the baseline signal is used to detect leaks in subsequent containers.

In an example of the system, the variation in optical signal from one time to another on the same container is used to detect a leak.

In an example of the system, the concentration of gas inside the container is determined.

In an example of the system, the absolute or relative pressure of gas inside the container is determined.

In an example of the system, a measure of the size of a leakage is determined by measuring continuously or repeatedly an optical signal and determining the rate of change of the signal.

It should be noted that the use of the terms "first part" and "second part" in the previous description must not be interpreted as meaning that these two steps must be carried out in sequential order. The actions described in the second part may in some situations be carried out before, simultaneously with, or after the actions described in the first part, or combinations of these.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which.

DESCRIPTION OF EXAMPLES

Figure 1:
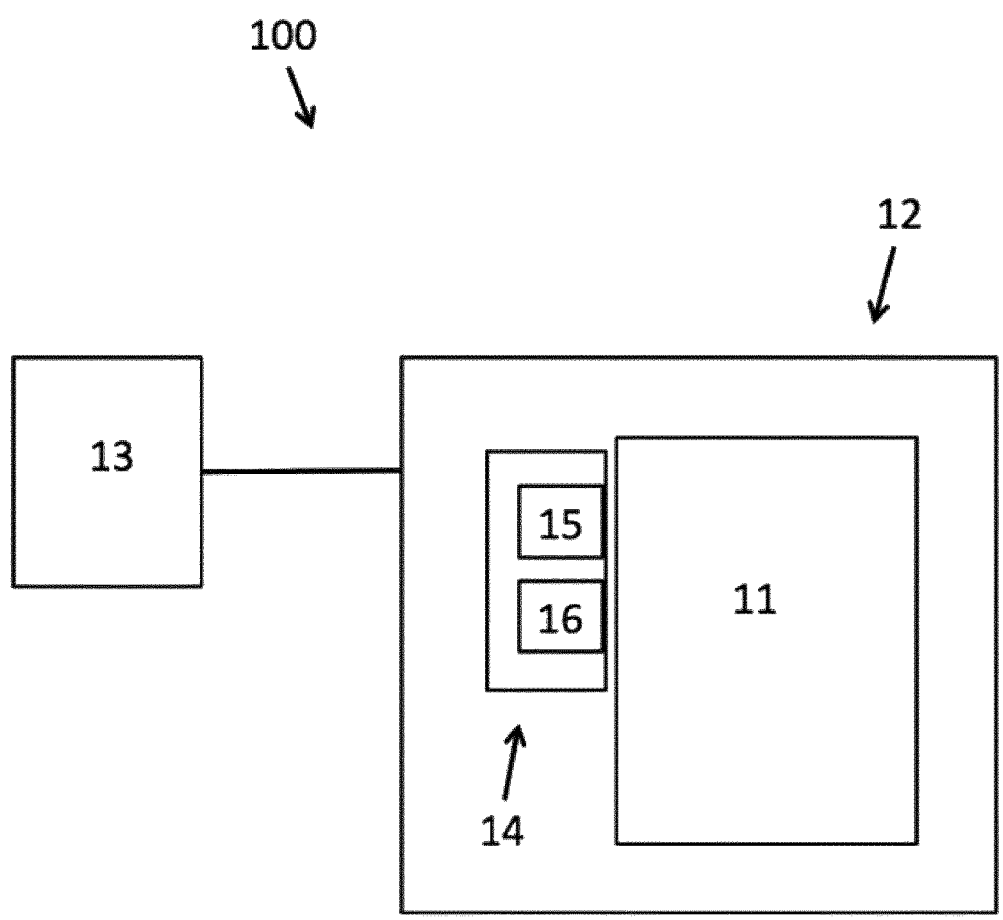
FIG. 1 is illustrating an example of a system and method to determine the integrity of a sealed container.

Specific examples of the disclosure will now be described with reference to the accompanying drawings. This disclosure may, however, be embodied in many different forms and should not be construed as limited to the examples set forth herein; rather, these examples are provided so that this disclosure will be thorough and complete, and will fully convey the scope of the disclosure to those skilled in the art.

The following disclosure focuses on examples of the present disclosure applicable to determining the integrity of containers, by subjecting the containers to variations in outside atmosphere and performing optical measurements on the container. For example, this is advantageous for detecting leaks in a package. However, it will be appreciated for the person skilled in the art that the description is not limited to this application but may be applied to many other systems where the integrity of containers needs to be determined.

The disclosure generally comprises the combination of two parts, where the first part comprises of subjecting the container to variations in outside pressure or gas composition, such as by placing it in a (partial) vacuum or underpressure, or exerting overpressure on the container with atmospheric air or other gases, or combinations of these steps. When applying a change in gas concentration or gas composition to the surrounding of the container, and the applied pressure outside the container is about the same as the pressure inside the container, as a partial pressure change for a particular molecule present in the gas inside the container may still be achieved.

The purpose of changing a gas pressure, a gas composition, a gas concentration, or any combination of gas pressure, gas concentration and gas composition in a surrounding of the container is to impose change to the concentration, or composition, or pressure, of the gas or gases inside the container as result of any leaks in the container.

When performing a combination of changing the gas pressure, gas composition, or gas concentration, this may be done either simultaneously, for example by applying an over pressure or underpressure together with a change in gas concentration or composition. Alternatively, and/or alternatively, in some examples, the combination of the changes to the gas pressure, gas composition or gas concentration may be done sequentially, for example by in a first step applying an underpressure using one gas concentration or gas composition followed by a second step applying an overpressure with the same gas composition or gas concentration, or the other way round first applying an overpressure followed by an underpressure. In some examples different gas concentration or gas compositions are used in the first step and the second step. In another example, the pressure is the same in the first step and the second step only the gas concentration or gas composition is changed.

It is also possible to simultaneously apply different pressures for different molecules in the gas composition by applying a partial change in gas pressure for a particular molecule and a different partial pressure for another molecule, for example by changing the gas concentration or composition, one molecule may be exposed to a partial underpressure while a second molecule may be exposed to a partial overpressure.

The second part consists of subjecting the container to optical spectroscopic measurement of the gas or gases inside the container, with the purpose of detecting any variation in the optical signal arising as consequence of the leak as opposed to the signal where no leak is present. Such difference in signal could be due to, but is not limited to, a decreased or increase of the concentration of at least one gas inside the container as result of the leak, or a variation in the gas pressure inside the container, or the introduction of a new gas species inside the container due to the leak.

In an example illustrated in FIG. 1, a container 11 that has a certain amount of gas is subjected to an integrity test in the system 100, wherein it is placed in a surrounding 12. The surrounding may for example be an enclosure, a partial enclosure or an open surrounding. A pump 13 may be used to at least partially change the gas pressure, gas composition, gas concentration or a combination of these in the surrounding of the container. In case there is a leak in the container, the gas inside the container may leak out into the surrounding and/or gas in the surrounding may leak into the container. Thus an absolute concentration of the gas inside the container may change, as may the pressure inside the container. An optical sensor 14 is applied to the outside of the container, the sensor consisting of a light source 15 and a light detector 16. Preferably, the sensor is designed or adjusted to detect the spectroscopic signal of at least one of the gases that are present inside the container.

In some examples, the optical sensor consists of a sensor based on tunable diode-laser absorption spectroscopy (TDLAS).

In some examples, the optical sensor consists of a sensor for gas in scattering media absorption spectroscopy (GASMAS). The GASMAS technique may be used for investigating sharp gas spectral signatures, typically 10000 times sharper than those of the host material, in which the gas is trapped in pores or cavities, such as headspaces of a container. GASMAS combines narrow band diode laser spectroscopy, developed for atmospheric gas monitoring, with diffuse media optical propagation, well known from biomedical optics. Photons injected into a container from a narrow band optical source may be detected in transmission or in backscattering arrangements. The technique has also been extended to remote sensing applications (LIDAR GASMAS or Multiple Scattering LIDAR. One example of a GASMAS sensor system and detection principle is described in EP 10720151.9 (Svanberg et al.) which is herein incorporated by reference.

Figure 4:
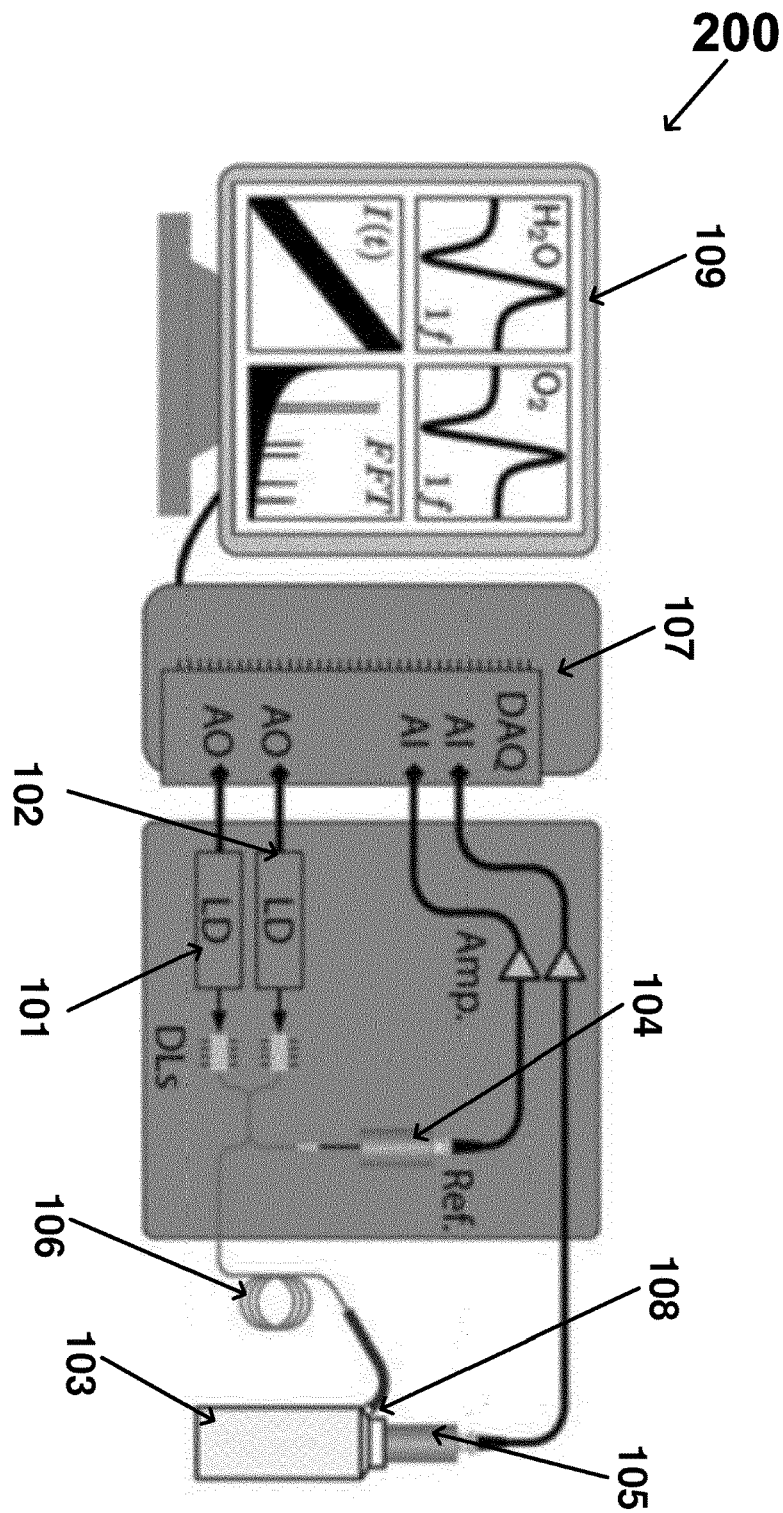
FIG. 4 is illustrating a schematic example of a gas sensing instrument for GASMAS techniques.

The gas sensing instrument 200 described in EP 10720151.9 is depicted in FIG. 4, and consists of two diode lasers drivers 101, 102, for monitoring oxygen and water vapour inside a container 103. Monitoring of other gases or more than two gases are possible depending on the wavelengths used. The light from the diode lasers (DLs) is brought together and separated into two fibres—one used to monitor the background (Ref.) and one sent to the sample (Probe), with reference 104 and probe 105 detector respectively. The two diode lasers may operate at the wavelengths were the container is translucent, making the GASMAS technique suitable. The laser light is guided to the sample 103 via optical fibres 106 and a hand held fibre head 108. The scattered light emerging out from the sample is acquired by a detector and the generated signal is sampled by a computer 107. In this example, wavelength modulation techniques are used to increase the sensitivity of the instrument by sinusoidally modulating the wavelength and studying the generated harmonics. In some examples, simultaneous detection of water vapour and oxygen is enabled by modulating at different frequencies. In this example, the first overtone (1$f$) illustrated on the monitor 109 in FIG. 4, was used for absorption evaluation.

The apparatus 200 may assess the containers without contacting the containers and instead detect the gas inside the packages from a remote distance. This is advantageous as the speed of detection may be increased and also for inline monitoring of containers.

The method described in EP 10720151.9 comprises emitting light from a narrow-band laser source towards the container from outside of the container. Measuring an absorption signal of the light scattered in the container, the absorption caused by at least one gas in the container when the light is scattered and travels in the container. The measuring is made outside of the container, and the assessment is non-intrusive with regard to the container.

Due to the scattering of the light in the sample a complication at the evaluation of the absorption signals obtained with the GASMAS method is the unknown gas interaction path length which the light has experienced.

The path length is important in traditional gas absorption spectroscopy for concentration quantification, as determined by the Beer-Lamberts law. Further details regarding how to perform the evaluation and interaction path length is disclosed in EP 10720151.9 and incorporated herein by reference.

Other types of GASMAS systems and methods are described in the article "Optical Analysis of Trapped Gas—Gas in Scattering Media Absorption Spectroscopy"; Svanberg, S; Laser Physics, 2010, Vol. 20, No. 1, pp. 68-77; ISSN 1054-660X, these systems and methods described therein are incorporated by reference. The GASMAS systems and methods are described in the article are illustrated in FIGS. 5A to 5C.

Studies of gas in scattering media are normally performed with CW laser sources giving rise to a time integrated gas signal. However, for monitoring the flow of photons through a sample, a time resolving measurement system may be useful. In FIG. 5A to 5C, experimental arrangements used in GASMAS studies are illustrated.

Figure 5A:
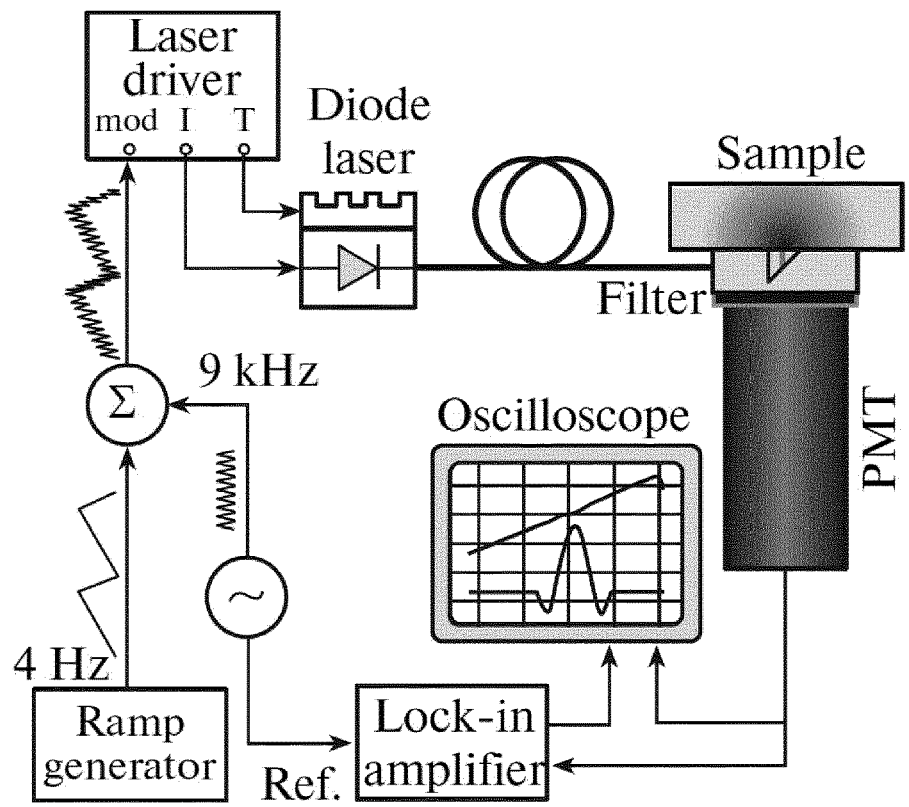
FIG. 5A to 5C are illustrating different schematic examples of gas sensing instruments for GASMAS techniques.

FIG. 5A is illustrating a system for wavelength modulation spectroscopy based on a single mode, few mW output power diode laser which is repetitively tuned across a gas absorption line by ramping the driving current. A backscattering arrangement is shown, where photons are collected by a large area photomultiplier tub. The second derivative of the absorption line is shown, as obtained by wavelength modulation of the laser and employing phase-sensitive lock-in detection. Alternatively, in some examples, the system may be arranged for transmission measurements.

Figure 5B:
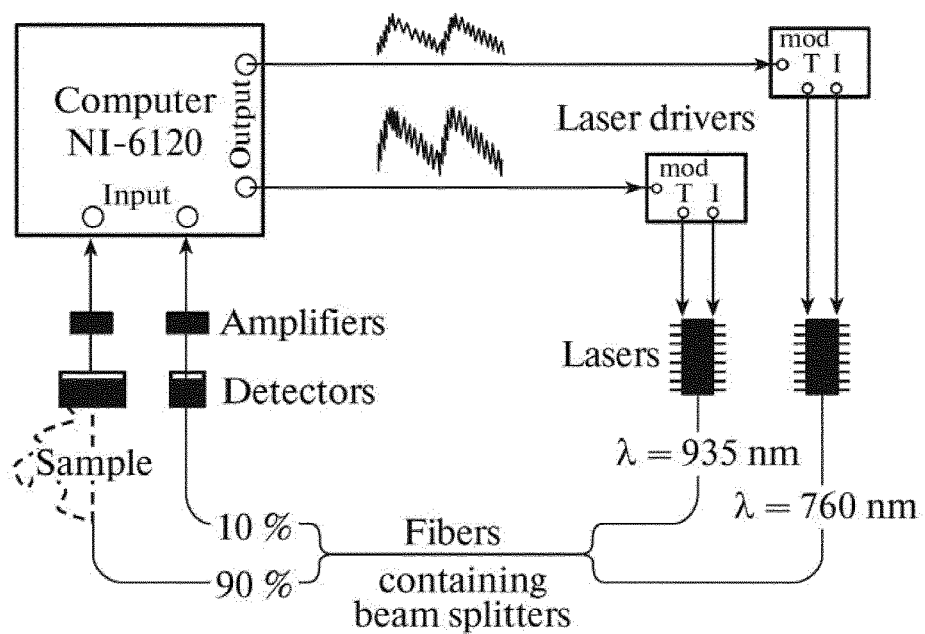
Figure 5C:
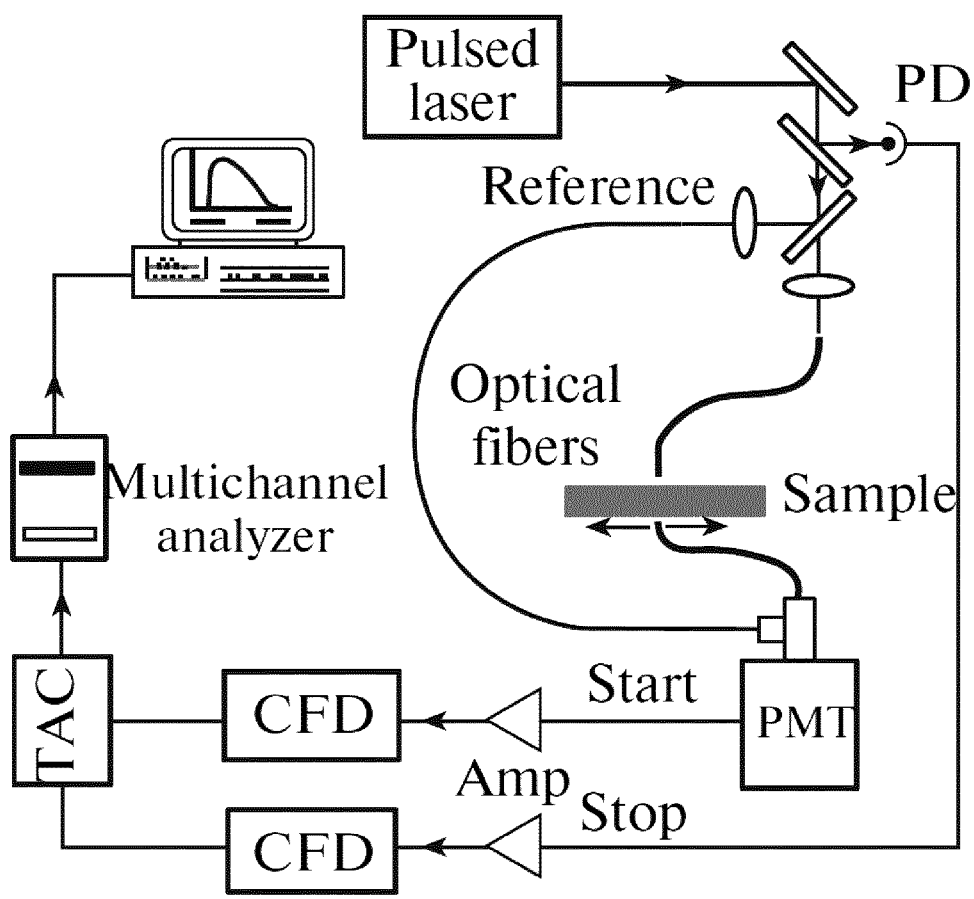

FIG. 5B is illustrating an implementation where two gases, for example, oxygen and water vapour are monitored simultaneously in transmission mode. Monitoring of other gases or more than two gases are possible depending on the wavelengths used. Alternatively, in some examples, the system may be arranged for backscattering measurements. A common detector is used, and the two signals are separated by phase-sensitive detection of the two spectroscopic signals, tagged with different modulation frequencies. Partial common fibre optical pathways may be used. The GASMAS signal which is recorded in, for example, arrangements such as those just described depends on the gas concentration in pores or headspaces, the gas, and on the effective path length through gas in the complex multiple scattering process. The strength of the recorded gas imprint is therefore generally expressed as an equivalent path length, Leq.

The mean path length through the scattering medium may be derived from time resolved measurements with a set-up such as the arrangement illustrated in FIG. 5C. Delayed coincidence single photon counting techniques are used to obtain the histogram of photon arrival times.

In some examples, the optical sensor consists of an LED light source and a photodetector.

In some examples, the optical sensor consists of a sensor for photoacoustical detection.

In some examples, the optical sensor consists of a sensor for Raman spectroscopy of the gas inside the container.

In some examples, the optical sensor consists of a broad wavelength light source and a spectrometer.

In some examples, the optical sensor consists of a sensor for laser-induced breakdown spectroscopy of the gas inside the container.

In some examples, the optical sensor is working in transmission mode, i.e., the light transmitter is located on one side of the container, and the light detector is located on the opposite side of the container, and a light beam is transmitted from the light transmitter through the container to the light detector.

In some examples, the optical sensor is working in reflection mode, i.e., the light transmitter is located on the same side of the container as the light detector, and the light detector records back-scattered light from the container.

In some examples, the light transmitter and the light detector are positioned in arbitrary positions in relation to each other on the container, and the light detector records scattered light from the container.

In some examples, the light is guided to and/or from the container by means of optical fibres. In some examples, the light is guided to and/or from the container via optical components including lenses, mirrors, windows, or other means of guiding and directing light.

The container must, at least partly, be made of a material that at least partly transmits light at a wavelength suitable for detection of the gas or gases. If there is a leak in the container, this is indicated by a difference in signal from the sensor for the leaking container compared to a similar container with no leak, or simply indicated by a difference in signal before and after the container is subjected to the partial vacuum. Alternatively, the signal from the sensor can be used to determine the absolute concentration or pressure of the gas inside the container, and that information is used to determine whether a leak is present or not.

Depending on the size of the leak one intends to detect, it may be preferable to wait some time after the change to the gas concentration, gas composition or gas pressure of the surrounding has been performed before performing the sensor measurement, to allow a sufficient amount of at least one gas present in the container or in the surrounding to leak out and/or out of the container. In some situations it may be advantageous to allow the optical sensor to measure continuously and analyse the rate of change of the signal, since this rate of change is a measure of the size of the leak.

Figure 2:
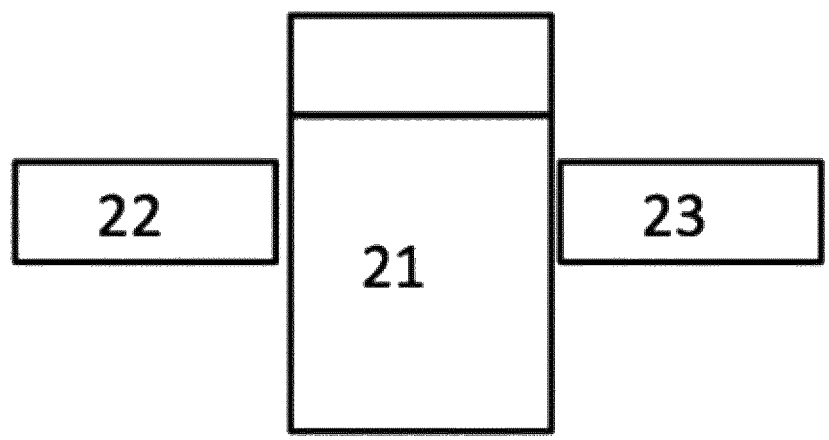
FIG. 2 is illustrating an example of a plastic pharmaceutical bottle that is subjected to a spectroscopic measurement.

In a particular example, an experiment was carried out where the method outlined in the previous sections was applied to pharmaceutical plastic bottles. A test bottle made of white plastic was prepared to have a leak with specific characteristics: a capillary tube with a diameter of 30 µm was inserted through the cap. The bottle was subjected to a measurement using a tunable diode-laser absorption spectroscopy sensor at 760 nm, to detect oxygen gas non-intrusively inside the bottle. The optical measurement provided a baseline signal of the oxygen gas inside the bottle. FIG. 2 depicts the measurement situation, where 21 shows the pharmaceutical bottle, 22 shows the laser transmitter, and 23 shows the light detector.

Figure 3:
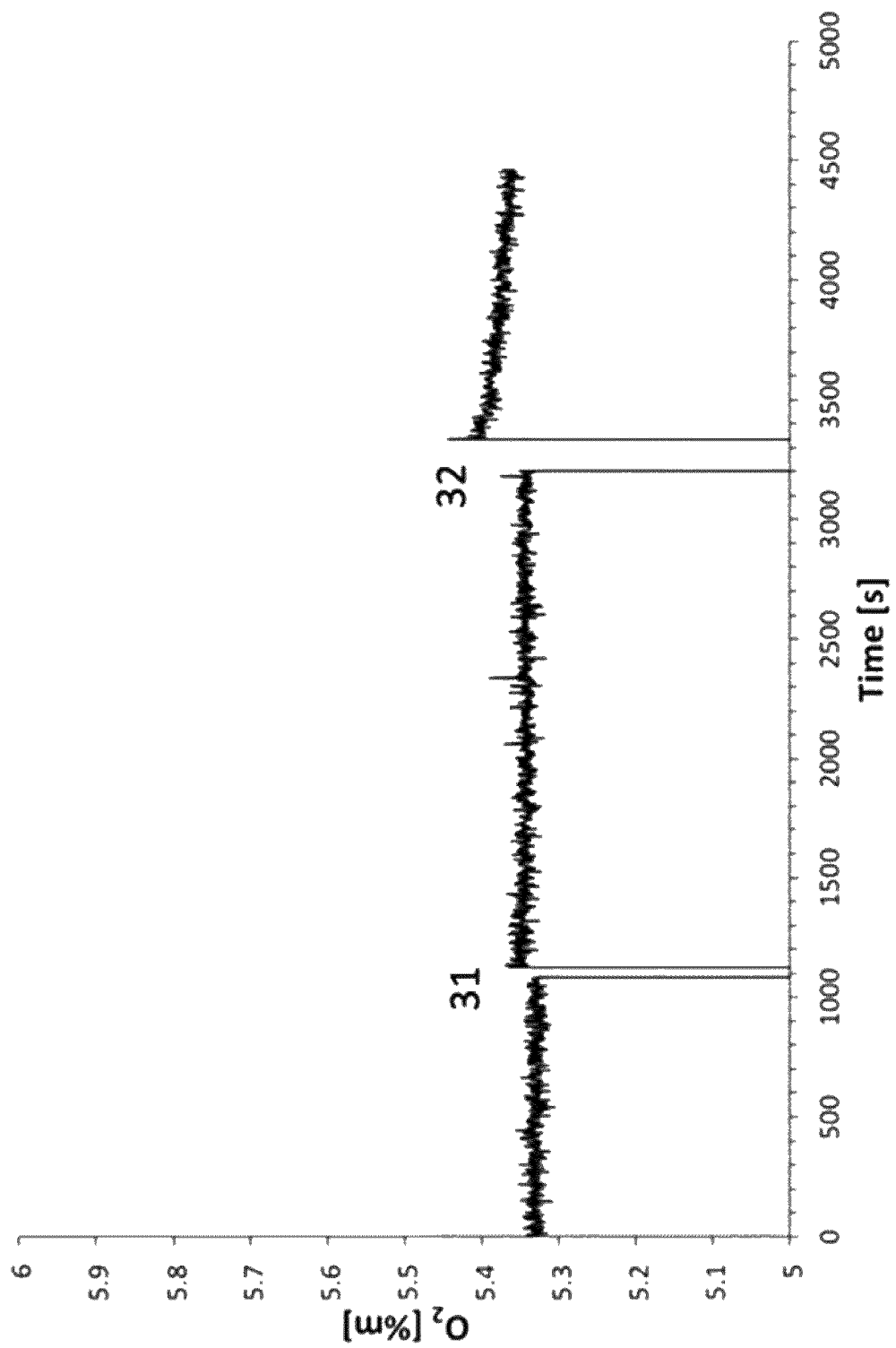
FIG. 3 is illustrating an example of the spectroscopic signal from oxygen gas inside a pharmaceutical bottle as it is subjected to external partial vacuum.

The bottle was then subjected to partial vacuum for 10 seconds, and then the optical measurement resumed. The effect of this is depicted in FIG. 3, which shows the spectroscopic oxygen signal (% meter) as a function of time (seconds). At the point 31, the 10-second vacuum took place. After the 10-second vacuum, there was an increase in the spectroscopic oxygen signal of 0.4%. The reason for the signal increasing, despite the fact that the oxygen pressure inside the bottle decreased as result of the surrounding vacuum, is that the decreased pressure causes a spectroscopic line-narrowing, which in turn causes an increase in the peak value of the line.

The bottle was subjected to vacuum again at point 32 in FIG. 3, this time for 30 seconds. At this point, there was a 1.2% increase in the spectroscopic signal. The experiment shows that the method of subjecting a pharmaceutical bottle to vacuum, in combination with a spectroscopic technique to detect the signal from oxygen gas inside the bottle, can be used to determine the presence of a leak in the bottle.

In another example, a container containing a gas, or mix of gases, is placed in an enclosure, and a measurement of the gas concentration inside the container is performed using an optical sensor consisting of a light source and a light detector. The measurement provides a baseline recording of the gas concentration inside the container. Then, the enclosure is at least partially evacuated of air. The enclosure is then filled with a gas composition different from air, such as nitrogen. Then, the gas concentration is again measured using the optical sensor. A lower reading compared to the baseline is indicative of a leak. An advantage of this example compared to performing the optical measurement in vacuum, or near vacuum, is that the spectroscopic linewidth of the gas inside the container is essentially the same, regardless of whether a leak is present or not, because the pressure is essentially the same. Thus, no spectroscopic linewidth correction is required due to differences in pressure.

In another example, a container containing a gas, or mix of gases is placed in an enclosure. Then, the enclosure is at least partially evacuated of air. The enclosure is then filled with a different gas (or gases) that is not initially present inside the container, or which is present at a known concentration. Then, a measurement of the concentration of the different gas inside the container is performed using an optical sensor consisting of a light source and a light detector. The presence of, or increased concentration of, the different gas inside the container is indicative of a leak. In some examples, the different gas may consist of carbon dioxide.

In another example the container is transported on a conveyance band through a surrounding being a partial enclosure, such as a tunnel, or a walled space. Inside this partial enclosure a pump may be used to apply a change to the gas pressure, gas composition, gas concentration or any combination thereof. The measurements may then be performed on the moving containers by having them passing an optical sensor either after it has passed through the partial enclosure or simultaneously. In the partial enclosure the container may pass through different sections having different gas pressures, gas concentrations, or gas compositions.

Alternatively, the container may pass through an open surrounding where a pump is used to apply a gas cloud for the container to pass through, for example by spraying a gas on the container. As previously described above, this may expose the container to a change in the gas concentration, gas composition, gas pressure or any combination thereof.

It should be noted that in the examples described above, it is not necessary to measure the gas concentration in absolute values. In some examples it is sufficient to measure a signal that is related to the gas concentration. In some examples, the spectroscopic signal is related to the gas pressure.

In some examples, at least one reference container is used, the reference container having no leaks, or having leaks with known characteristics. The measurement on the reference container provides a baseline signal which is used for comparison with the measured signals on subsequent containers.

The present invention has been described above with reference to specific examples. However, other examples than the above described are equally possible within the scope of the disclosure. Different method steps than those described above, performing the method by hardware or software, may be provided within the scope of the invention. The different features and steps of the invention may be combined in other combinations than those described. The scope of the disclosure is only limited by the appended patent claims.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases.

The invention claimed is:

1. A method of determining the integrity of a closed container, said method comprising:
   positioning said container in a surrounding;
   changing a gas pressure, a gas composition, a gas concentration, or any combination of gas pressure, gas concentration and gas composition, in said surrounding;
   subjecting said container to an optical sensor, non-intrusively, said sensor being sensitive to at least one gas, and said sensor is configured for detecting said at least one gas inside said container;
   reading a signal from said optical sensor related to a gas pressure, a gas concentration, a gas composition, or any combination of gas pressure, gas concentration, and gas composition, inside said container; the behaviour of said signal being indicative of breach in integrity of said container.

2. The method according to claim 1, in which a vacuum or underpressure is applied in said surrounding.

3. The method according to claim 1, in which overpressure is applied in said surrounding.

4. The method according to claim 1, in which a gas or mix of gases is applied in said surrounding.

5. The method according to claim 1, in which any combination of the following steps a)-c) is applied in sequence
   a) a vacuum or underpressure is applied in said surrounding,
   b) overpressure is applied in said surrounding, and
   c) a gas or mix of gases is applied in said surrounding.

6. The method of claim 1, in which said optical sensor is (i) based on any spectroscopic or optical means of gas detection or (ii) based on tunable diode laser absorption spectroscopy (TDLAS) or (iii) based on gas in scattering media absorption spectroscopy (GASMAS).

7. The method of claim 1, in which a reference container which is known not to have leaks, or to have leaks of known characteristics, is used to provide a baseline signal, and the difference in optical signal compared to said baseline signal is used to detect leaks in subsequent containers.

8. The method of claim 1, in which the variation in optical signal from one time to another on the same container is used to detect a leak.

9. The method of claim 1, in which the concentration of gas inside the container is determined or in which the absolute or relative pressure of gas inside the container is determined.

10. The method of claim 1, in which a measure of the size of a leak is determined by measuring continuously or repeatedly an optical signal and determining the rate of change of said signal.

11. A system for determining the integrity of a sealed container, said system comprising:
    a surrounding configured for positioning said container, said surrounding is configured for changing a gas pressure, a gas composition, a gas concentration, or any combination of gas pressure, gas concentration, and gas composition;
    a non-intrusive optical sensor sensitive to at least one gas, and said sensor is configured for detecting said at least one gas inside said container;
    a control unit for reading a signal from said optical sensor related to a gas pressure, a gas concentration, a gas composition, or any combination of gas pressure, gas concentration, and gas composition, inside said container; the behaviour of said signal being indicative of breach in integrity of said container.

12. The system according to claim 11, in which a vacuum or underpressure is applied in said surrounding.

13. The system according to claim 11, in which overpressure is applied in said surrounding.

14. The system according to claim 11, in which a gas or mix of gases is applied in said surrounding.

15. The system according to claim 11, in which any combination of the following steps a)-c) is applied in sequence
    a) a vacuum or underpressure is applied in said surrounding,
    b) overpressure is applied in said surrounding, and
    c) a gas or mix of gases is applied in said surrounding.

16. The system of claim 11, in which said optical sensor is (i) based on any spectroscopic or optical means of gas detection, or (ii) based on tunable diode laser absorption spectroscopy (TDLAS), or (iii) based on gas in scattering media absorption spectroscopy (GASMAS).

17. The system of claim 11, in which a reference container which is known not to have leaks, or to have leaks of known characteristics, is used to provide a baseline signal, and the difference in optical signal compared to said baseline signal is used to detect leaks in subsequent containers.

18. The system of claim 11, in which the variation in optical signal from one time to another on the same container is used to detect a leak.

19. The system of claim 11, in which the concentration of gas inside the container is determined or in which the absolute or relative pressure of gas inside the container is determined.

20. The system of claim 11, in which a measure of the size of a leak is determined by measuring continuously or repeatedly an optical signal and determining the rate of change of said signal.

* * * * *